(12) United States Patent
Varkiani et al.

(10) Patent No.: US 8,350,095 B2
(45) Date of Patent: Jan. 8, 2013

(54) METHOD FOR THE PRODUCTION OF DIMETHYL ETHER

(75) Inventors: Hossein Manafi Varkiani, Tehran (IR); Kambiz Zadeh Sadaghiani, Tehran (IR); Hamid Reza Bakhtyari, Tehran (IR); Hamid Reza Godini, Kermanshah (IR); Laleh Shirazi, Tehran (IR); Akbar Zamaniyan, Tehran (IR); Mahmoud Khakpour, Tehran (IR)

(73) Assignee: RIPI, Tehran (IR)

( * ) Notice: Subject to any disclaimer, the term of this patent is extended or adjusted under 35 U.S.C. 154(b) by 715 days.

(21) Appl. No.: 12/221,892

(22) Filed: Aug. 6, 2008

(65) Prior Publication Data
US 2009/0048468 A1 Feb. 19, 2009

(30) Foreign Application Priority Data
Aug. 7, 2007 (EP) .................... 07113965

(51) Int. Cl.
*C07C 41/09* (2006.01)
*C07C 43/04* (2006.01)
*C07C 61/00* (2006.01)

(52) U.S. Cl. ........................ 568/698; 568/699

(58) Field of Classification Search ............ None
See application file for complete search history.

(56) References Cited

U.S. PATENT DOCUMENTS

| | | | | |
|---|---|---|---|---|
| 3,039,941 A | * | 6/1962 | Sweeney et al. | 203/2 |
| 5,037,511 A | * | 8/1991 | Dornhagen et al. | 203/37 |
| 5,684,213 A | | 11/1997 | Nemphos et al. | |
| 5,705,711 A | | 1/1998 | Preston | |
| 5,817,906 A | * | 10/1998 | Marker et al. | 585/640 |
| 2009/0069607 A1 | * | 3/2009 | Smith et al. | 568/671 |

FOREIGN PATENT DOCUMENTS

| | | | |
|---|---|---|---|
| DE | 3225732 A1 | * | 1/1984 |
| EP | 0407038 | | 1/1991 |
| KR | 2006040210 A | * | 5/2006 |
| WO | 93/19032 | | 9/1993 |
| WO | 97/30960 | | 8/1997 |

OTHER PUBLICATIONS

Sundmacher et al. (Eds.) "Reactive Distillation Status and Future Directions." 2002, Wiley-VCH Verlag GmbH & Co. KGaA.

* cited by examiner

*Primary Examiner* — Rosalynd Keys
(74) *Attorney, Agent, or Firm* — Behravesh & Richmond, PLLC

(57) ABSTRACT

Provided is a process for the production of dimethyl ether. The process improves the effectiveness of the production of dimethyl ether. Especially, the process can be combined with processes for the production of methanol.

12 Claims, 1 Drawing Sheet

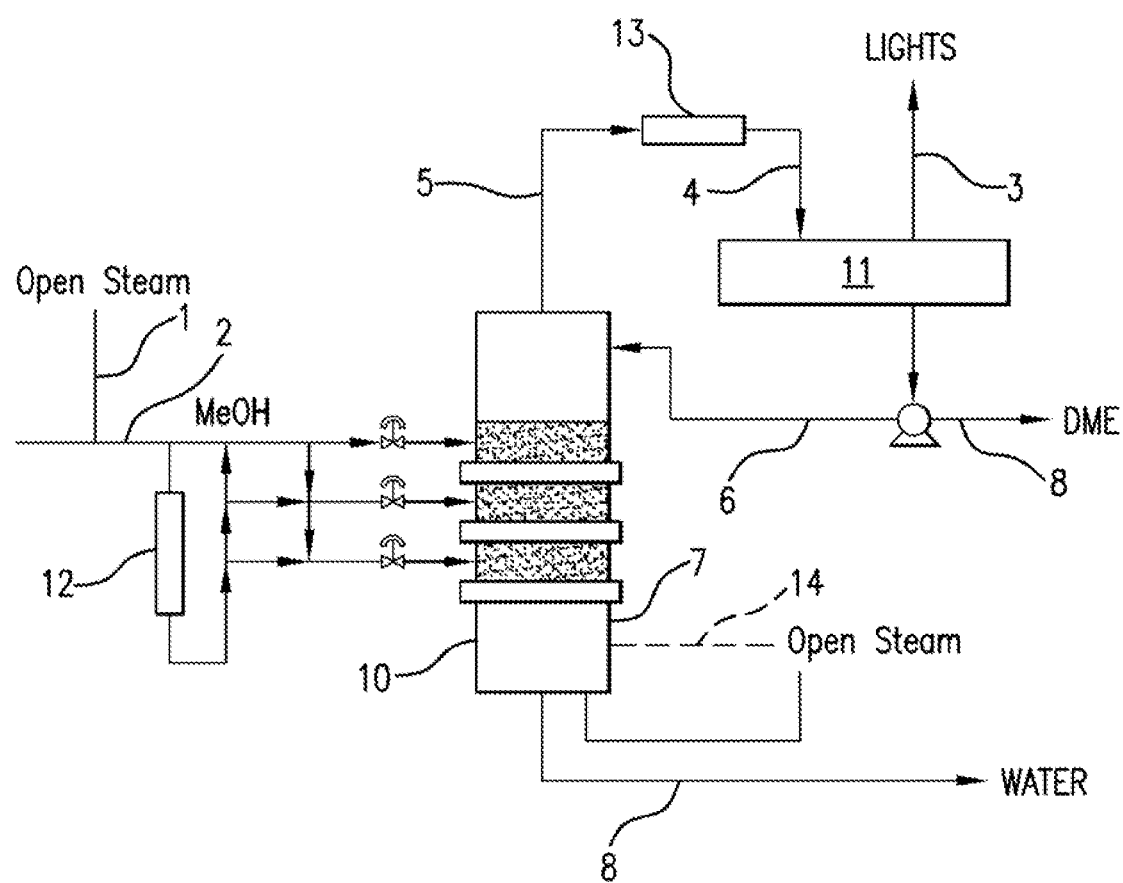

METHOD FOR THE PRODUCTION OF DIMETHYL ETHER

CROSS REFERENCE

The present application claims benefit of EP 07 113965.3 filed on Aug. 7, 2007, whose content is incorporated herein by reference.

BACKGROUND OF THE INVENTION

The present invention relates to a method for the production of dimethyl ether (DME). DME can be used as a solvent and also as an intermediate in the synthesis of other compounds.

The method considered here is the dehydration of methanol using the so-called reactive distillation (RD) system. In an RD system both the production and purification of DME are performed simultaneously in one single reactor/distillation tower, which is technically entitled a reactive distillation column (Reactive Distillation Status and Future Directions, Sundmacher, Kai/Kienle, Achim, 1. Edition—December 2003, ISBN-13: 978-3-527-30579-7-Wiley-VCH, Weinheim).

The dehydration of methanol to produce DME through an RD system is disclosed, e.g., in the documents EP 407 038 A (Smith et al.) and U.S. Pat. No. 5,684,213 (Nemphos et al.).

EP 407 038 A discloses the application of a variety of acidic catalysts under different temperature and pressure conditions. In their work a stream of alkyl alcohols enters a middle section of the RD tower, where the reaction takes place over a catalyst bed and the separation is performed at the same time. The overhead comprising DME is condensed in a condenser and fed to an accumulator. The bottoms portion is primarily water. A reboiler is provided to recycle a portion of the bottom.

U.S. Pat. No. 5,684,213 suggests a process almost similar to that mentioned above with the exception that an $H_2$ stream was used to increase the efficiency of the system. The operating conditions for a group of alkyl ethers were mentioned to be 130-300° C. and 140 to 6800 kPa.

The concentration of DME is controlled at the top of the tower by adjusting the reflux ratio, and at the bottom the temperature was controlled via adjusting the amount of "reboiled ratio" by controlling the amount of used steam.

U.S. Pat. No. 5,705,711 A refers to a process for the production of methyl tert.-butyl ether by dehydration of methanol and tert butanol. The process described in this patent application does not refer to the production of DME.

For determination of the optimum system design at any section of the RD tower the simultaneous consideration of the effects of operational and kinetic parameters is required. For example, adjusting the tower pressure involves changing the operational temperature of the tower. The same is true with regard to the conditions of the condenser, reboiler and their utilities. In previous works, a variety of operational temperatures and pressures, and the amount of the reflux ratio were addressed.

In using RD for the production of DME through the previously mentioned systems, the complex interaction of the effective factors is a drawback, and hence, any measures taken to simplify the system will be valuable.

In the control systems according to the art, the amount of the reflux stream is used to adjust the product concentration. The amount of the reboiled stream, which is controlled by the amount of steam used in the reboiler, is used to adjust the reaction bed temperature. Known RD tower control systems are complicated and hence expensive.

Due to different operating conditions and concentrations of liquid or gas phases, the combination of the prior art processes to produce dimethyl ether with processes for the production of methanol is highly complicated.

Furthermore, the methods according to the prior art consume high amounts of energy.

SUMMARY OF THE INVENTION

In one embodiment the present invention provides a process for the production of dimethyl ether comprising the steps of:
(a) feeding a first stream containing methanol into a pre-reactor with a fixed bed solid acidic catalytic structure thereby, catalytically reacting at least a portion of methanol to form dimethyl ether and water;
(b) feeding at least a part of the product of the pre-reactor to a distillation column reactor as a stream in liquid and/or gaseous phase;
(c) contacting said stream containing methanol with a fixed bed solid acidic catalytic structure in a distillation reaction zone, thereby catalytically reacting at least a portion of methanol to form dimethyl ether and water;
(d) fractionating the resultant dimethyl ether product from water and unreacted material;
(e) withdrawing the dimethyl ether product from the distillation column reactor as a first stream containing dimethyl ether, and
(f) withdrawing water and unreacted material as a second stream.

The stream of the pre-reactor can be split into at least two sub-streams and fed into the distillation column reactor at different feeding zones. The product stream of the pre-reactor to the distillation column reactor can comprise 20 to <100 wt. % methanol. A second stream containing methanol can be added to the distillation column reactor. A gaseous phase can be used. The pre-reactor and/or the distillation column reactor can comprise an acidic resin. The pressure in the distillation column reactor can be in the range of 8 to 10 bars. The temperature in the reaction zone of the distillation column reactor can be in the range of 130 to 150° C. A portion of the first stream containing dimethyl ether can be returned as reflux. The process can be carried out with at least one outlet for a gas. The process can further comprise a condenser for condensing the dimethyl ether product from the distillation column reactor and the outlet for a gas is positioned within or after the condenser. An open steam can be fed at the bottom of the distillation column reactor instead of a reboiler. An open steam can be used to heat the feed of the distillation column reactor. The process can be combined, with a process for producing methanol.

BRIEF DESCRIPTION OF THE FIGURES

FIG. 1 is the structure of a reactive distillation tower.

DETAILED DESCRIPTION OF THE INVENTION

An object of the present invention is to provide a method for a more effective production of dimethyl ether. Furthermore, it is an object of the present invention to provide a process for the production of dimethyl ether, which can easily be controlled. Another object of the present invention is to have higher levels of control over stabilization of the concentration, pressure, flow rates, and temperature in the methanol production plant and other plant having the ability to serve as a feed supply.

An additional object of the present invention is to provide a process for the production of dimethyl ether, which can easily be combined with methods for preparation of methanol. These methods are of particular interest in situations such as GTF (gas to fuels) processes in which methanol streams with different levels of purity are yielded at the middle and end of the process.

Still further it is an object of the present invention to provide a process for the production of dimethyl ether, which needs only low amounts of energy and hence is also cost efficient.

The process of the present invention can be combined with processes for producing methanol. The combination of a process according to the present invention with a process for producing methanol entails improvements with regard to energy consumption and simplification of the whole process.

The process according to the present invention provides a product having a high purity.

The pre-reactor used in the present invention allows the use of the different liquid phase concentrations by converting some of the methanol present in the feed stream to products and, hence, adjusting the concentration of the stream to the optimum values required by the operational conditions of the RD tower.

Furthermore, using a pre-reactor allows decreasing the reaction zone size of the RD column.

According to a special embodiment of the present process, eliminating the non-condensable gaseous species simplifies the integration of the dimethyl ether production with other processes at any desired points.

According to an embodiment of the present invention, an improvement can be achieved through taking measures that help handle the non-condensable gases and concentration changes of various streams.

In this regard, integrating RD-DME production process with blocks of other processes like non-FT GTL (gas to liquids) is of great importance. Such integration requires the ability of RD-DME production units to handle feeds of different concentrations of methanol. To integrate the RD process with other units (regarding the characteristics of the streams between different units) the present process makes the system compatible with streams of different concentrations and also handling the accompanying non-condensable gas streams.

A further improvement can be achieved by feeding gaseous streams, e.g. open steam, at the bottom of the tower and by using two or more feeds comprising different amounts of methanol. As a result of preheating by open steam and using open steam as a reboiled stream, other apparatus like some of the heat exchangers in the feed section and reboilers can be eliminated. Furthermore, the features mentioned above make the system more flexible towards the water content of the feed and increase the controllability of the system.

According to a preferred embodiment of the present invention, by feeding gaseous streams, e.g. open steam at the bottom part of the tower, the control system can be simplified. This way the tower temperature can be controlled by controlling the rate of the entrance of steam at the bottom of the tower. This is done through injecting open steam under or over the liquid surface, more preferably under the liquid surface. According to another embodiment of the invention, the open steam is injected under the liquid surface by means of a nozzle installed in a proper position. Furthermore, by injecting all or a fraction of the steam into the feed stream, the required feed heating can be achieved to some extent, without using heat exchangers or through using a few of them, and without causing any concentration and/or temperature instabilities in the next sections.

The product concentration can be controlled by returning at least a portion of the first stream containing dimethyl ether as reflux. This makes the RD tower control parameters simpler and as a result, by taking measures like opening or closing the waste stream valve and controlling the liquid level in the tower, one can control the RD system easily. Preferably, the reflux ratio is in the range of 5 to 9.

Taking the above measures it will be possible to use the streams of raw methanol (with different gas or liquid concentrations of methanol and/or non-condensable species) as a feed for the RD-DME process. As a result it reduces and/or eliminates the apparatus and utilities required for purification(s), pressure adjustment(s) and separation(s) of gaseous species. For an example, apparatus such as flash tank(s), pump and heat exchangers can be eliminated. Not only will this result in a process with less equipment, but it will also undergo less sequential temperature and pressure changes in comparison to the previous systems.

In addition to the general capabilities resulted from the mentioned features, the operational conditions of the tower can be adjusted in order to use cooling water, and low-to-high pressure steam available in the plant. Preferably middle pressure steam, and the cooling water available in the plant, can be used as utilities for simultaneous heating and cooling of the system, respectively.

As a result, some of the equipment usually used in prior art systems (reboiler and heat exchanger(s)) can be replaced by feeding gaseous streams, e.g. open steam; and if integrated with another process, pumps and related equipment, a purge gas scrubber, a flash tank for the purged gases, a distillation tower for methanol and the related equipment) could be eliminated. Furthermore, the operational costs of the integrated unit are also reduced due to overcoming the sequential pressure and temperature changes occurring in conventional systems. Based on what is said, the operational conditions of the present invention are more optimized for the production of DME through methanol dehydration using the RD method. It should be noted that, integrating the conventional processes to methanol units would result in sever sequential changes in the temperatures, pressures and concentrations. Therefore operating costs of the general processes, which use this invention, will be reduced.

As mentioned above, in the process of the present invention a first stream containing methanol is fed into a pre-reactor with a fixed bed solid acidic catalytic structure thereby catalytically reacting at least a portion of methanol to form dimethyl ether and water.

According to a preferred embodiment, the pre-reactor may comprise one, two, three or more outlets where the reacted liquid stream can exit in some desired points along the pre-reactor. Using such preferred pre-reactor enables an adjustment of the composition being fed to the RD column.

Furthermore, the pre-reactor preferably comprises catalytic structures being able to handle DME vapor such as Bale packing.

Preferably, a methanol-containing stream can be added as a gaseous phase to the pre-reactor. The first feed of methanol can comprise 20 to 100% by weight, preferably 80 to 100% by weight of methanol.

The pre-reactor comprises a fixed bed solid acidic catalytic structure catalyst. Such catalysts are known in the art. These catalysts include, e.g. acidic resins and molecular sieves. Useful molecular sieves include porous crystalline, three-dimensional alumina-silicates of the zeolite mineral group.

These catalysts are described, e.g., in U.S. Pat. No. 5,684,213 and EP-A-0 407 038. Preferably the catalyst is an acidic resin, such as temperature-tolerated catalysts like Amberlyst™ 35 (Rohm and Haas, Philadelphia, Pa.).

At least a part of the product stream of the pre-reactor is fed to a distillation column reactor. The feed stream feeding the RD tower preferably comprises 20 to 100 by weight of methanol, more preferably 80 to 90% by weight, and 0 to 50% by weight of DME, preferably 0.1 to 5%. If the concentrations of the mentioned components in this feed stream do not suit the conditions of the RD tower, they are fed into the pre-reactor, so that the contents of the stream are suited for processing in the RD tower, afterwards. If the feed stream is initially suited to enter the RD tower, the stream is not fed to the pre-reactor. That feed is contacted with a fixed bed solid acidic catalytic structure in a distillation reaction zone thereby catalytically reacting at least a portion of methanol to form dimethyl ether and water. The obtained product mixture is fractionated within the distillation column.

Preferably, the temperature of said product stream of the pre-reactor being fed to the distillation column reactor is in the range of 120 to 150° C., more preferably in the range of 125° C. to 135° C. The product of the pre-reactor can be fed to the column as a gaseous phase.

Furthermore, at least a part of a second methanol-containing stream being obtained from the distillation column reactor can be returned to the distillation column reactor. Preferably, the second methanol-containing stream can be added as a gaseous phase. Preferably, the second methanol-containing stream comprises a lower methanol content than the product stream of the pre-reactor being fed to the distillation column reactor. According to a preferred embodiment of the present invention, the weight ratio of the product stream of the pre-reactor being fed to the distillation column reactor to the second stream containing methanol is preferably in the range of 1.5 to 3.3, more preferably in the range of 2.5 to 3.2. Preferably, the temperature of second stream containing methanol being fed to the distillation column reactor is in the range of 120 to 220° C., more preferably in the range of 150° C. to 220° C. The second methanol-containing stream being obtained from the distillation column reactor can be injected below the liquid surface being formed at the bottom of the distillation column reactor. The stream resulting from the mixing of the second feed of methanol and the first feed can comprise 20 to <100% by weight, preferably 80 to 90% by weight of methanol.

According to a preferred embodiment of the present invention, the stream of the pre-reactor can be split into at least two sub-streams and fed into the distillation column reactor at different feeding zones. That embodiment improves the controllability of the present system by adjusting the reaction temperature.

Furthermore, the distillation column reactor can be fed with a methanol feed which has not been reacted in the pre-reactor, but is directly fed to the distillation column reactor. Preferably, the methanol feed being not reacted in the pre-reactor comprises a higher methanol content than the product stream of the pre-reactor being fed to the distillation column reactor.

As mentioned above, a gaseous stream comprising methanol can be fed to the distillation column reactor. Preferably, the gaseous stream is injected below the liquid surface being formed at the bottom of the distillation column reactor.

The manner of operating the distillation column reactor, i.e., the severity of the conditions, is determined by the Operator to achieve the desired result. The pressure of the column is increased until the desired extent of reaction is obtained. Preferably, the pressure in the distillation column reactor is in the range of 8 to 10 bars. The temperature of the reaction system depends on the applied pressure. Preferably, the temperature in reaction zone of the distillation column reactor is in the range of 130 to 150° C. The distillation column reactor comprises a fixed bed solid acidic catalytic structure. Either the acid cation exchange resins or molecular sieves described above may be used for the reaction. Examples of such catalysts are mentioned in the documents as stated above. Preferably, bale packing catalyst are used.

In this reaction both the ether product and water must be removed to force the reaction to completion. The water is removed as bottoms, with possible alcohol contamination, and the dimethyl ether as overhead. The recovery of the product in this embodiment is relatively simple since water does not form an azeotrope with dimethyl ether.

Usually, the system comprises a condenser for condensing the dimethyl ether product from the distillation column reactor. The gaseous products of the distillation column are preferably condensed at a temperature in the range of 30° C. to 50° C., more preferably 37° C. to 45° C. Preferably, the system comprises at least one outlet for a gas being positioned within or after the condenser. The outlet for a gas can be used to withdraw gases, which are not condensed in the condenser. Such gases will be expressed as "non-condensable gases". The non-condensable gases can be used as fuels or as reactants in the production of other compounds.

A reflux is preferably included in the system. The reflux ratio could vary over the rate of 0.5 to 25:1, preferably 5:1 to 9:1. In practice, the higher ratio may be used to compensate for a short catalyst bed.

Another advantage of this embodiment is that the alcohol can be substantially removed from the water leaving as bottoms by operating the lower portion of the tower to distill the alcohol from the water. This may reduce the pass-through in the distillation tower-reactor, which is more than offset by the elimination of other distillation towers to recover the alcohol from the water once it leaves the reactor.

According to a preferred embodiment, the process is combined with a process for producing methanol.

A preferred process for producing dimethyl ether according to the present invention is illustrated in FIG. 1. The system includes a pre-reactor (12) a reactive distillation (RD) column (10), a condenser (13) and a gas liquid separation tank (11) with an outlet for a gas (3) as mentioned above.

According to the process shown in FIG. 1, a gaseous stream comprising methanol, e.g. open steam, is used as heating stream. The gaseous stream comprising methanol has a pressure in the range of 800 to 1400 kPa. The gaseous stream provides a reboiled stream at the bottom of the tower (stream 14) and heats the feed stream (stream 2). The heating the feed stream can be achieved by using either open steam or heat exchanger (stream 1).

A pre-reactor, packed with either the same catalyst as the RD-DME tower or with a different one can be used to adjust the feed concentrations at optimum values. According to a preferred embodiment of the present invention, said pre-reactor is packed with acidic resins.

The condensation system makes it possible to supply the reflux stream and the produced DME at a temperature equal to the equilibrium boiling point of the mentioned streams under the operating pressure, in the form of liquid streams of desired purities.

The non-condensable gases leave the system either through stream 3 or through any proper stream leaving the condenser.

At the bottom of the tower, the open steam plays the role of the stripping stream (stream 14). The product at the bottom of the tower is an aqueous stream containing some unconverted Methanol and its purity is controlled (by using different amounts of steam and different degrees of steam super-saturation) at a permitted level for off-loading and further refinement operations.

The packed bed of the RD-DME tower used in the process of FIG. 1 is in the form of so called Bale packing, which comprises of sewed cloth packs containing acidic resin catalysts or other proper catalysts.

The optimum hydrodynamic conditions are applied for adjusting the temperature and concentration profiles throughout the RD tower, where "the optimum hydrodynamic conditions" refers to the amount of reflux stream (stream 6), the amount of reboiled streams entering the tower (stream 14) and splitting ratio(s) of the feed stream(s) entering the tower.

The optimum range for the reflux stream at the top of the tower is found to be 5-9. Tuning the tower pressure (in the range of 8-10 bar) and adjusting the DME reflux stream (stream 6), optimizes the corresponding temperature at different points of the tower. The optimum temperature in the enrichment section is in the range of 38-130° C., in the stripping section is in the range of 150-170° C. and in the reaction section is in the range of 130-150° C. Using the Bale packing catalyst bed makes it possible to use a wide range of gas and liquid traffic in the tower, without facing problems of flooding or the dryness of the bed.

Using a pump (FIG. 1) the methanol feed (stream 2) reaches the optimum pressure (8-10 bars). This can also be achieved by using high-pressure methanol streams from the methanol plant. In order to reach the required feed temperature (which is the equilibrium boiling temperature under the operational pressure), gaseous stream comprising methanol is injected in the feed stream. Any combinations of open steams and other heating systems may also be used for this purpose.

The feed having concentrations of 20-100% by wt. of methanol, preferably 80-90% by wt. reaches the optimum reaction conditions. Once the pressure reaches 8-10 bars, the other operational conditions are set at their optimum value according to the specific design of the different parts of the system. This is achieved through using a pre-reactor and splitting the feed, which are easily applicable for a wide range of feed conditions.

Depending on the methanol concentration in the feed, a portion or all of the feed enters a pre-reactor and then goes to the RD-DME tower. After entering the pre-reactor (12), the feed concentration changes and the conditions of the pre-reactor can be set so that the concentration reaches the optimum value required for the RD-DME process. This is achieved by converting some of the methanol in the feed to DME. Regarding the amount of methanol and water in the feed, and to better utilize the catalyst bed, the treated feed, leaving the pre-reactor is split to two or more sub-streams (e.g. streams 2' and 3") which enter the RD tower from one or more desired points so that the stable operation of the tower is maintained through using the hydrodynamic-concentration factors. To adjust the concentration of the components to the amounts compatible with the gas liquid traffic, the procedure below is used.

If the methanol concentration is low in the feed stream, the feed enters the tower via the lower branches without using the open steam. If the methanol concentration is high in the feed stream, the feed is entered the tower via the upper branches along with using the open steam.

The stream leaving the top of the tower (stream 5) is liquefied in the condenser as a product stream (13) and a portion of it is recycled (as reflux ratio) (6) to the RD column (10). The rest is stored as the product.

The separation takes place in a gas-liquid tank (11), either as an independent device or as a part of the condenser (13).

The reboiled stream is supplied in the form of a portion of the product at the bottom of the tower, which mainly consists of water, and can be vaporized by means of open steam.

It is also possible that the open steam is injected above the liquid surface, without passing through the liquid and plays the role of the reboiled stream.

The invention also relates to the following items:

1. An improved process for the production of dimethyl ether comprising the steps of:
   (a) feeding a first stream containing methanol into a pre-reactor with a fixed bed solid acidic catalytic structure thereby catalytically reacting at least a portion of methanol to form dimethyl ether and water,
   (b) feeding at least a part of the product stream of the pre-reactor to a distillation column reactor,
   (c) contacting said stream containing methanol with a distillation structure in a distillation reaction zone thereby catalytically reacting at least a portion of methanol to form dimethyl ether and water, and
   (d) fractionating the resultant dimethyl ether product from water and unreacted material,
   (e) withdrawing the dimethyl ether product from the distillation column reactor as a first stream containing dimethyl ether, and
   (f) withdrawing water and unreacted material as a second stream. is provided. Furthermore, the problem is solved by the following items:
2. The process according to item 1 wherein said product stream of the pre-reactor is fed to the distillation column reactor as a liquid and/or gaseous phase.
3. The process according to item 1 and/or 2 wherein said stream of the pre-reactor is split into at least two sub-streams and fed into the distillation column reactor at different feeding zones.
4. The process according to at least one of the preceding items wherein said product stream of the pre-reactor being fed to the distillation column reactor comprises 20 to <100 wt. % methanol.
5. The process according to at least one of the preceding items wherein said product stream of the pre-reactor being fed to the distillation column reactor comprises 0 to 50 wt. % dimethyl ether.
6. The process according to at least one of the preceding items wherein the temperature of said product stream of the pre-reactor being fed to the distillation column reactor is in the range of 120 to 150° C.
7. The process according to at least one of the preceding items wherein a second stream containing methanol is added to the distillation column reactor.
8. The process according to item 7 wherein the second stream containing methanol is added as a gaseous phase.
9. The process according to item 7 or 8 wherein the temperature of said second stream containing methanol is in the range of 150 to 220° C.
10. The process according to at least one of the items 7 to 9 wherein the weight ratio of said product stream of the pre-reactor being fed to the distillation column reactor to the second stream containing methanol is in the range of 1.5 to 3.3.
11. The process according to at least one of the preceding items wherein the pre-reactor comprises an acidic resin as a fixed bed solid acidic catalytic structure.

12. The process according to at least one of the preceding items wherein the pressure in the distillation column reactor is in the range of 8 to 10 bars.
13. The process according to at least one of the preceding items wherein the temperature in the reaction zone of the distillation column reactor is in the range of 130 to 150° C.
14. The process according to at least one of the preceding items wherein at least a portion of the first stream containing dimethyl ether is returned as reflux.
15. The process according to any of the above items wherein the catalyst used in the distillation column reactor is an acidic resin.
16. The process according to at least one of the preceding items wherein the system comprises at least one outlet for a gas.
17. The process according to item 16 wherein the system comprises a condenser for condensing the dimethyl ether product from the distillation column reactor and the outlet for a gas is positioned within or after the condenser.
18. The process according to at least one of the preceding items wherein a gaseous stream comprising methanol is injected below the liquid surface being formed at the bottom of the distillation column reactor.
19. The process according to any of the above items wherein the process is combined with a process for producing methanol.

What is claimed is:

1. A process for the production of dimethyl ether comprising the steps of:
   (a) feeding a first stream containing methanol into a pre-reactor with a fixed bed solid acidic catalytic structure thereby, catalytically reacting at least a portion of methanol to form dimethyl ether and water;
   (b) feeding at least a part of the pre-reactor product to a distillation column reactor in liquid and/or gaseous phase;
   (c) contacting said product containing methanol with a fixed bed solid acidic catalytic structure in a distillation reaction zone, thereby catalytically reacting at least a portion of methanol to form dimethyl ether and water;
   (d) fractionating the resultant dimethyl ether product from water and unreacted material;
   (e) withdrawing the dimethyl ether product from the distillation column reactor as a first stream containing dimethyl ether, and
   (f) withdrawing water and unreacted material as a second stream; and
   (g) combing the process with a process for producing methanol;
   wherein the pre-reactor comprises at least two outlets; and wherein the product of the pre-reactor is split into at least two sub-streams and fed into the distillation column reactor at different feeding zones.

2. The process according to claim 1 wherein said product of the prereactor being fed to the distillation column reactor comprises 20 to <100 wt. % methanol.

3. The process according to claim 1 wherein a second stream containing methanol is added to the distillation column reactor.

4. The process according to claim 3 wherein a gaseous phase is used.

5. The process according to claim 1 wherein the pre-reactor and/or the distillation column reactor comprise an acidic resin.

6. The process according to claim 1 wherein the pressure in the distillation column reactor is in the range of 8 to 10 bars.

7. The process according to claim 1 wherein the temperature in the reaction zone of the distillation column reactor is in the range of 130 to 150 degree C.

8. The process according to claim 1 wherein at least a portion of the first stream containing dimethyl ether is returned as reflux.

9. The process according to claim 1 wherein the process is carried out with at least one outlet for a gas.

10. The process according to claim 9 wherein the process further comprises a condenser for condensing the dimethyl ether product from the distillation column reactor and the outlet for a gas is positioned within or after the condenser.

11. The process according to claim 1, wherein an open steam is fed at the bottom of the distillation column reactor instead of a reboiler.

12. The process according to claim 1 wherein an open steam is used to heat the feed of the distillation column reactor.

* * * * *